(12) United States Patent
Lamoureux et al.

(10) Patent No.: US 12,082,675 B2
(45) Date of Patent: Sep. 10, 2024

(54) HANDPIECE FOR A MEDICAL OR COSMETIC PROCESSING DEVICE

(71) Applicant: NWT MANAGEMENT GMBH, Taucha (DE)

(72) Inventors: Bruno Lamoureux, Brussels (BE); Dieter Bauch, Jockgrim (DE); André Paufler, Leipzig (DE)

(73) Assignee: NWT MANAGEMENT GMBH, Taucha (DE)

( * ) Notice: Subject to any disclaimer, the term of this patent is extended or adjusted under 35 U.S.C. 154(b) by 529 days.

(21) Appl. No.: 17/426,063

(22) PCT Filed: Jan. 29, 2020

(86) PCT No.: PCT/EP2020/052155
§ 371 (c)(1),
(2) Date: Jul. 27, 2021

(87) PCT Pub. No.: WO2020/157125
PCT Pub. Date: Aug. 6, 2020

(65) Prior Publication Data
US 2022/0095763 A1 Mar. 31, 2022

(30) Foreign Application Priority Data

Jan. 29, 2019 (DE) ............ 10 2019 102 179.0

(51) Int. Cl.
*A45D 29/00* (2006.01)
*A61C 1/05* (2006.01)
(52) U.S. Cl.
CPC .............. *A45D 29/00* (2013.01); *A61C 1/05* (2013.01)

(58) Field of Classification Search
CPC ........ A45D 29/00; A45D 29/05; A45D 29/14; A45D 2200/1054; A61C 1/05; A61C 1/10;
(Continued)

(56) References Cited

U.S. PATENT DOCUMENTS 3,631,597 A * 1/1972 Lieb .................. A61C 1/14
279/54
4,033,039 A * 7/1977 Lohn .................. A61C 1/14
433/129
(Continued)

FOREIGN PATENT DOCUMENTS

DE 3311193 A1 10/1984
DE 3402585 A1 8/1985
(Continued)

*Primary Examiner* — Mohamed G Gabr
*Assistant Examiner* — Aman Kumar Mann
(74) *Attorney, Agent, or Firm* — Olson & Cepuritis, Ltd.

(57) ABSTRACT

The invention relates to a handpiece (100) for a medical or cosmetic processing device, having:—a connection line (102) at a connection end (101); and—a housing (104) in which a receiving area is provided between the connection end (101) and the processing end (103), a rotary drive unit being receivable in said receiving area in order to drive a rotary tool (210) which can be attached to the processing end (103). The invention is characterized in that the handpiece (100) can be separated from the connection end (101), wherein the handpiece (100) is designed such that the motor (110) remains on the connection end (101) after uncoupling the housing (104), and the handpiece has a rotary clamping device (120) in which the rotary tool (210) can be attached.

20 Claims, 5 Drawing Sheets

(58) Field of Classification Search
CPC .. A61C 1/147; A61C 1/06; A61C 1/08; A61C 1/14; A61C 19/004; A61C 1/18; A61C 1/088; A61C 17/20; A61C 1/144; A61B 2090/0813; A61B 17/54
See application file for complete search history.

(56) References Cited

U.S. PATENT DOCUMENTS

| | | | | |
|---|---|---|---|---|
| 4,040,311 | A * | 8/1977 | Page, Jr. | B23B 31/2025 |
| | | | | 433/132 |
| 5,040,979 | A * | 8/1991 | Kuhn | A61C 1/14 |
| | | | | 433/126 |
| 6,126,442 | A * | 10/2000 | Knorpp | A61C 1/06 |
| | | | | 433/133 |
| 6,149,430 | A * | 11/2000 | Nemetz | A61C 1/05 |
| | | | | 433/125 |
| 6,186,783 | B1 * | 2/2001 | Brassil | A61C 17/08 |
| | | | | 433/91 |
| 7,214,060 | B2 * | 5/2007 | Ma | A61C 1/147 |
| | | | | 433/128 |
| 9,119,690 | B2 * | 9/2015 | Rauchenzauner | A61C 1/05 |
| 2014/0199654 | A1 * | 7/2014 | Schwarzbraun | A61C 1/12 |
| | | | | 606/1 |
| 2018/0125622 | A1 * | 5/2018 | Almoumen | A61C 1/0023 |

FOREIGN PATENT DOCUMENTS

| | | |
|---|---|---|
| DE | 19652190 A1 | 7/1997 |
| DE | 202004005966 U1 | 7/2004 |
| DE | 102006023187 A1 | 1/2007 |
| DE | 102007030019 A1 | 2/2009 |
| DE | 202014007414 U1 | 10/2014 |
| EP | 0670149 A1 | 9/1995 |
| EP | 0920839 A2 | 6/1999 |
| EP | 1362559 A1 | 11/2003 |
| EP | 1970020 A1 | 9/2008 |
| EP | 2664288 B1 | 3/2016 |

* cited by examiner

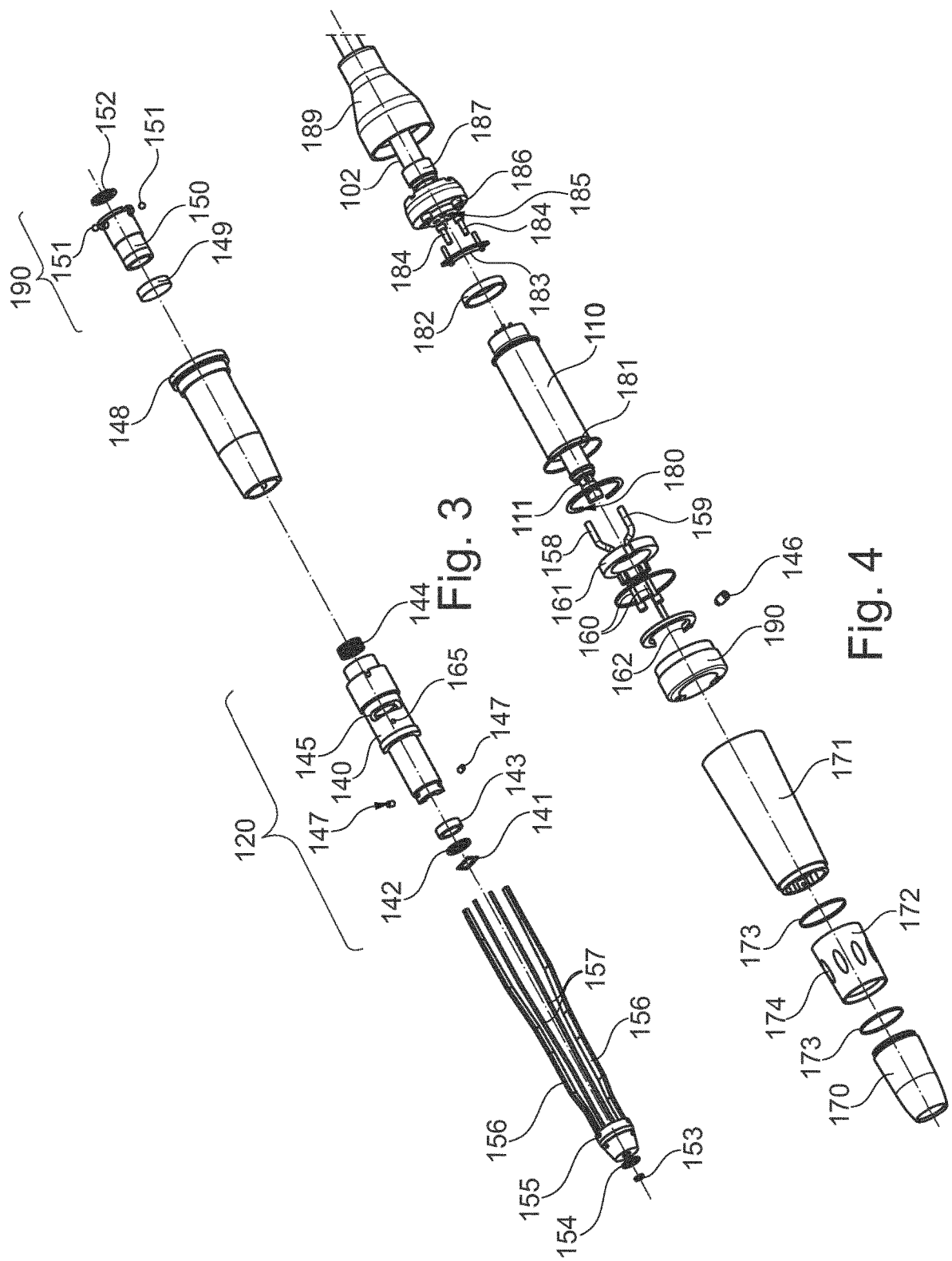

HANDPIECE FOR A MEDICAL OR COSMETIC PROCESSING DEVICE

CROSS-REFERENCE TO RELATED APPLICATIONS

This application is a U.S. National Stage of PCT/EP2020/052155, filed Jan. 29, 2020, claiming priority to DE Application No. 102019102179.0 filed Jan. 29, 2019, both of which are incorporated herein by reference.

FIELD OF THE INVENTION

The invention relates to a handpiece for a medical or cosmetic processing device, having a connection line at a connecting end; a housing in which a receptacle space is provided between a connecting end and a processing end, a rotary drive unit for driving a rotary tool that is attachable to the processing end being able to be received in said receptacle space. The handpiece is designed such that said handpiece is able to be separated from the connecting end, wherein the motor as part of the rotary drive unit remains in particular on the connecting end and the detachable part of the handpiece is able to be separately sterilized, in particular sterilized by heat or steam. The handpiece furthermore has a novel rotary clamping device in which the rotary tool is able to be attached.

BACKGROUND TO THE INVENTION

Devices for removing, for example, callused skin on feet or hands, are used in personal hygiene, the callused skin being milled or sanded off using these devices. The tools are operated at a high rotating speed. Apparatuses having a similar fundamental construction are used in the medical sector, such as for example the dental sector. In order for a positive handling of the tool to be obtained, the known apparatuses are constructed in such a manner that one part of the apparatus receives a transformer and a rotating speed controller as well as the electronic components and a container, for example a bag or similar, for receiving the milled or sanded dust, and that this part of the apparatus is connected to a handpiece by way of a line section. An electric motor, typically a low-voltage motor, by way of which the driving of the tool takes place, is disposed in this handpiece.

The known devices have various disadvantages. As a result of a rigid connection, or a fixed anchoring, of the tool, for example by way of a mounting which is loaded by a compression spring, between the clamping unit and the motor unit, the handle is not able to be separated from the motor unit. In other known devices, the mounting of the tool takes place in a laborious manner by tightening a clamping element while using a separate tool. In the known devices, the suctioning takes place by way of ducts disposed in the handpiece, and is thus established as a result of the dimensions of the ducts. The known devices have the disadvantage that said known devices as a result of the construction thereof can be repaired only with relatively great complexity and, as a result of the disposal of the dust suctioning ducts, require a handpiece which is relatively large in the diameter, said devices thus becoming unwieldy. A further particular disadvantage as a result of the non-separable connection between the motor and the clamping unit mentioned above is that the handpieces cannot be cleaned and sterilized by heat or steam in a satisfactory manner, and the hygienic requirements required for treating different people with the same handpiece can thus not be met.

DE 3311193 A1 describes a device for foot care, in which the handpiece is indeed able to be separated from the device. Upon separation however, the motor unit is situated so as to be fixedly installed in the handpiece, as a result of which this handpiece thus designed is not able to be sterilized by heat or steam.

EP 2664288 B1 discloses a motor handpiece of a processing apparatus for chiropody or cosmetic foot care, for surgical use, or for the dental sector. This motor handpiece has a receptacle space in which an electric motor as well as a mounting for driving a tool that is able to be attached to the processing end are contained. That part of the handpiece that is able to be separated from the remainder of the device contains a fixedly installed motor, as is described in EP 2664288 B1, and is thus not able to be sterilized by heat or steam.

DE 202004005966 U1 also discloses a handpiece for a medical or cosmetic processing apparatus which within a housing has a rotary drive unit, wherein this housing is releasably connected to the remainder of the housing body by means of a bayonet fitting, for example. In the handpiece described here, the rotary drive unit conjointly with the motor also remains in that part of the handpiece that is able to be detached from the remainder of the device. The handpiece disclosed in DE 202004005966 U1 is thus also not able to be sterilized by heat or steam.

DESCRIPTION OF THE INVENTION

The object of the invention hence was to overcome the disadvantages of the prior art and to provide in particular a handpiece for a medical or cosmetic processing device which is simple to clean and able to be sterilized by heat or steam, and which enables rotary tools to be replaced in a simple comfortable manner without an additional tool.

This object is achieved by a handpiece for a medical or cosmetic processing device according to claim 1.

The handpiece according to the invention has a connection line at a connecting end; a housing in which a receptacle space is provided between a connecting end and a processing end, a rotary drive unit for driving a rotary tool that is attachable to the processing end being able to be received in said receptacle space. The handpiece is designed such that said handpiece is able to be separated from the connecting end, wherein the motor as part of the rotary drive unit remains in particular on the connecting end, and the detachable part of the handpiece is able to be separately sterilized, in particular sterilized by heat or steam. The handpiece furthermore has a novel rotary clamping device in which the rotary tool is able to be attached.

The handpiece according to the invention is able to be used in the sectors of pedicure, foot care, dental surgery, in the dental laboratory, or in any other sector in which the abrasion of a material is required. The rotation of a rotary tool such as a milling bit, grinding bit or a drill bit, requires a rotating mechanical drive which is generated by an electric motor or air. The rotary tool is held in the handpiece by mechanical clamping system. The handpiece according to the invention for driving the rotary tool preferably contains a micro-motor which is electrically operated. The handpiece is able to be detached from the connecting end, and thus from the micromotor situated at the connecting end. In a preferred embodiment, the micromotor is also able to be separately detached from the connecting end and thus from the connection line. During use, the abrasion generated by the rotary tool in some cases causes dust and/or heat. In practice, devices are used which either contain appliances for removing the created dust by suctioning during the use of the handpiece, or which contain appliances which have a spraying appliance by way of which the dust arising during the use is bound by means of a liquid, and cooling of the location of the treatment can simultaneously take place. The two embodiments of the devices used in practice often also contain an elimination device in order to guarantee the visibility of the treatment of the location to the user while using the handpiece. The handpiece according to the invention always has a novel rotary clamping device which is the subject matter of the present invention. The rotary clamping device is able to be installed both in handpieces which have a micromotor with suctioning, as well as in handpieces which have a micromotor with a spraying appliance and illumination appliance.

The rotary drive unit of the handpiece according to the invention has a motor, preferably an electric motor, particularly preferably an electrically operated micromotor. A further component part of the rotary drive unit is a bearing sleeve in which the rotary clamping device is able to be received. The rotary clamping device in the direction of the connecting end has a coupling which is releasably connected to the motor shaft and which in the direction of the processing end has a collet chuck in which the rotary tool is able to be attached. The coupling at the connecting end of the rotary clamping device in one preferred embodiment is a dog clutch which engages in a correspondingly shaped counterpart on the motor shaft of the motor of the rotary drive unit and thus enables a transmission of torque by way of a form-fit.

A further aspect of the invention relates to a rotary clamping device which enables a rotary tool in the handpiece according to the invention to be replaced in a simple manner. To this end, the rotary clamping device has appliances such as, for example a spindle sleeve, in which in the direction of the processing end of the handpiece the collet chuck is able to be received, and which in the direction of the connecting end of the handpiece contains a coupling to the motor shaft of the motor of the rotary drive unit. The spindle sleeve is preferably mounted in two ball bearings which on the rotary clamping device are provided in the direction of the connecting end of the handpiece and in the direction of the processing end. The collet chuck and the coupling are in each case connected, or able to be connected, respectively, to the spindle sleeve so as to be axially displaceable within an elongate bore by means of a clamping sleeve. The collet chuck is axially pre-loaded in relation to the spindle sleeve by means of tension spring. The coupling is mounted so as to be axially resilient and in the direction of the connecting end pre-loaded in relation to the spindle sleeve by means of a compression spring.

The rotary clamping device according to the invention enables in a simple manner to clamp a rotary tool or release the latter for replacing. To this end, the rotary clamping device in the direction of the connecting end has correspondingly suitable means which enable a rotating movement of the housing of the handpiece to be transmitted to the rotary clamping device in the interior of the handpiece and therein to be converted to an axial movement of the collet chuck. In one embodiment of the invention, this is implemented by a release unit which is a component part of the rotary clamping device. This release unit in a particularly preferred embodiment is composed of two parts, a sliding sleeve and the rotary sleeve. The sliding sleeve and the rotary sleeve have in each case mutually opposite congruent helicoids with identical gradients. The rotary sleeve and the sliding sleeve are mutually twisted by rotating the rotary sleeve, and an axial displacement of the collet chuck within the rotary clamping device is generated as a result. This results in the collet chuck being tensioned or relaxed and thus to a rotary tool being fastened in or released from the collet chuck. A suitable means for transmitting the rotating movement from the housing to the release unit of the rotary clamping device is preferably an entrainment pin which can be introduced into an opening of the rotary sleeve provided to this end. This entrainment pin can be, for example, a metal pin or a metal bolt, which is screwed into an opening of the rotary sleeve provided to this end. The rotary clamping device preferably has further means which prevent any conjoint rotation of the collet chuck when rotating the release unit. The rotary clamping device according to the invention has the advantage that a very simple but optimal tight clamping of a rotary tool can be performed. The rotary clamping device can be embodied such that a rotation of the clamping actuator takes place by up to 270°. It has however been demonstrated that it suffices for the clamping actuator to perform a rotation of up to 180°, preferably of up to 90°. An optimal tight clamping of the rotary tool in the collet chuck is guaranteed by way of a rotation of 90°.

The rotary clamping device according to the invention in one particularly preferred embodiment is embodied as a stand-alone unit, as a result of which the entire rotary clamping device of the handpiece according to the invention is retrievable and thus replaceable. In order for this to be guaranteed, the rotary clamping device in the direction of the connecting end of the handpiece can have further seals, locking elements and fastening elements.

In a preferred embodiment of the invention the rotary clamping device is disposed in a bearing sleeve in the interior of the housing of the handpiece, wherein the rotary clamping device in the direction of the processing end and in the direction of the connecting end of the handpiece is locked, fastened and mounted by means of locking elements, fastening elements and bearings. Establishing the extent, or the rotational angle, respectively, of the rotating movement of the rotary sleeve of the rotary clamping device is advantageously achieved in a very simple manner. The bearing sleeve in which the rotary clamping device is disposed has an elongate bore for guiding the entrainment pin which is connected to the rotary sleeve of the rotary clamping device in the interior of the bearing sleeve. The disposal of the entrainment pin and the dimensions of the elongate bore establish the extent of the rotating movement of the rotary sleeve of the rotary clamping device. The rotary sleeve is preferably rotatable by 90°, as described above.

As has already been described, a particular advantage of the handpiece according to the invention lies in that the handpiece without the motor can be decoupled from the connecting end in order that improved cleaning and sterilizing, in particular sterilizing by heat, can take place. For this reason, the bearing sleeve at the end directed toward the connecting end of the handpiece preferably has means for coupling or decoupling, respectively, the handpiece to/from the connecting end. These here can be customary bayonet devices, snap-fit closures or a screw connection. The connecting end preferably has correspondingly matching counterparts.

The handpiece according to the invention in an embodiment of the invention can be configured as a spray handpiece. In this case, the handpiece has appliances for conducting water and compressed air, and optionally light. The conduction of water and compressed air can take place by way of ducts, tubes or hoses. The conduction of light preferably takes place by way of light conductors. These means for conducting water, compressed air and light at the processing end of the handpiece open into a nose which has means for sealing, as well as an air nozzle and a water nozzle. The light conductor likewise opens into this nose. The means for conducting water, compressed air and light are guided in the interior of the housing of the handpiece and past the bearing sleeve on the outside of the latter. The connecting end which is connected to the connection line contains corresponding appliances by way of which the means for conducting water, light, and compressed air can be connected such that the conduction of water, light and compressed air from the connection line up to the nose and to the nozzles, that is to say from the connecting end up to the processing end of the handpiece, is guaranteed. Such a means can be a multiple coupling element, for example, in which individual couplings are contained for connecting supply lines for water, compressed air, electricity and light, in a bundled manner with the means for conducting the respective media through the handpiece provided to this end. It can also be provided that water and compressed air are conducted jointly as a spray fluid in a line, duct, tube or hose through the handpiece and at the processing end of the handpiece open into a single spray nozzle. A cooling effect of the operating region is achieved by the spray liquid conducted through the handpiece, on the one hand. Cooling of the motor in the handpiece is however also simultaneously achieved.

When the handpiece according to the invention is configured as a spray handpiece, the housing preferably has a plurality of parts, particularly preferably three parts, wherein the central part is configured as a rotatable sleeve. The entrainment pin which is disposed in the interior on the rotary sleeve of the release unit, engages in a depression which is provided to this end in the interior of the clamping ring of the housing. By rotating the clamping ring, the rotation of the rotary sleeve of the release unit in the rotary clamping device simultaneously takes place in the interior handpiece of the invention, as a result of which the collet chuck is able to be tensioned or released, and a rotary tool can be clamped or released. It is particularly preferable for the central rotatable sleeve to have recessed grips. As a result thereof, the handling of the handpiece according to the invention is improved, and it can be avoided that the user when tensioning and relaxing the collet chuck, that is to say while rotating the central sleeve, loses his/her grip by virtue of moisture which is present or dust which is present.

In a further embodiment of the invention the handpiece can be configured as a vacuum handpiece. In this case, a vacuum hose connector for connecting a suctioning hose is disposed on the connecting end.

In the embodiment as a vacuum handpiece, a rotary clamping device which is identical or similar to the rotary clamping device of the spray handpiece is fundamentally provided. The vacuum handpiece in the interior likewise has means for transmitting the rotating movement of the housing to the rotary clamping device. In the embodiment as a vacuum handpiece, the housing is preferably integrally designed as an outer a sleeve. When the outer sleeve is rotated, the entrainment pin which is disposed on the rotary sleeve of the release unit of the rotary clamping device and engages in the appliances of the housing provided to this end, is entrained and a rotating movement of the rotary sleeve is generated. The vacuum handpiece in the interior can have further means and devices which participate in transmitting the rotating movement from the housing to the rotary clamping device. Further elements by way of which the outer sleeve is able to be anchored to the rotary clamping device or further components in the interior of the housing can be provided. The collet chuck is able to be tensioned or released by the rotating movement of the outer sleeve, as a result of which a rotary tool can be clamped or released. The fastening of the housing, that is to say of the outer sleeve, to the connecting end in the case of the vacuum handpiece takes place by conventional means, such as a bayonet fitting device, for example, a releasable latching connection, a screw connection, or similar.

Provided for the removal of grinding dust and material abrasion during the operation of the vacuum handpiece is a vacuum duct in the interior of the handpiece, said vacuum duct passing through all portions of the handpiece as well as the motor portion up to the vacuum hose, so as to achieve suctioning by way of this passage duct. A suctioning appliance is usually connected to the vacuum hose.

It is a common feature of the spray handpiece and the vacuum handpiece that the motor of the rotary drive unit remains connected to the connecting end, and the housing of the handpiece without the motor can be decoupled from the connecting end. To this end, the handpiece in a further embodiment has a housing portion for the coupling device described above, by way of which the handpiece can be released from the connecting end or be connected to the connecting end.

A further advantage of the handpiece according to the invention lies in that the motor is designed such that the latter as a separate component is able to be detached from the connecting end in a simple manner. It is thus possible for the connecting end to be optimally cleaned and optionally sterilized and for the motor unit to be repaired or replaced. Devices for the embodiment of the releasable fasting of the motor to the connecting end are known to the person skilled in the art.

The materials of which the individual components of the handpiece according to the invention and of the rotary clamping device according to the invention are composed are preferably able to be sterilized, in particular sterilized by heat or steam. Suitable metals such as stainless steel, as well as suitable heat-resistant plastics materials such as, for example, polyether ether ketone (PEEK) are thus to be considered for the construction of the handpiece according to the invention.

The invention will be described in more detail hereunder by means of eight figures in which:

FIG. 3 shows details of the construction of a spray handpiece;

FIG. 4 shows details of the construction of a spray handpiece;

Figure 1A:
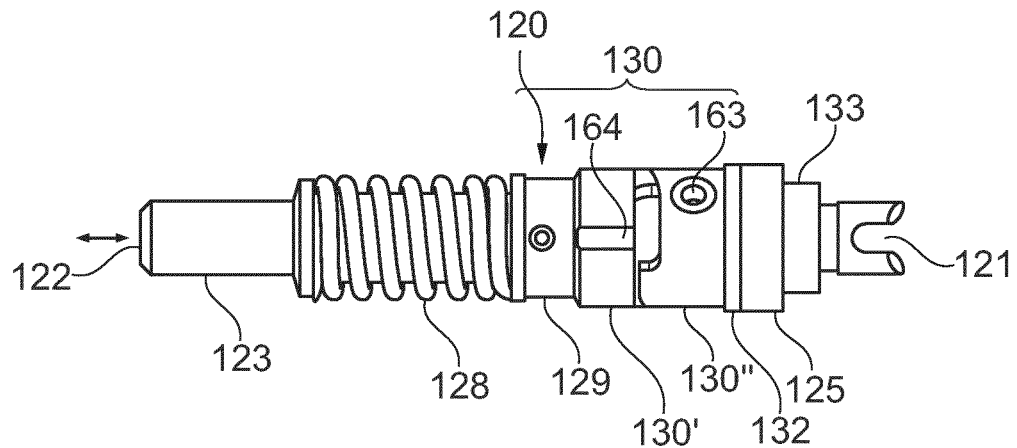
FIG. 1 shows the rotary clamping device according to the invention
Figure 1B:
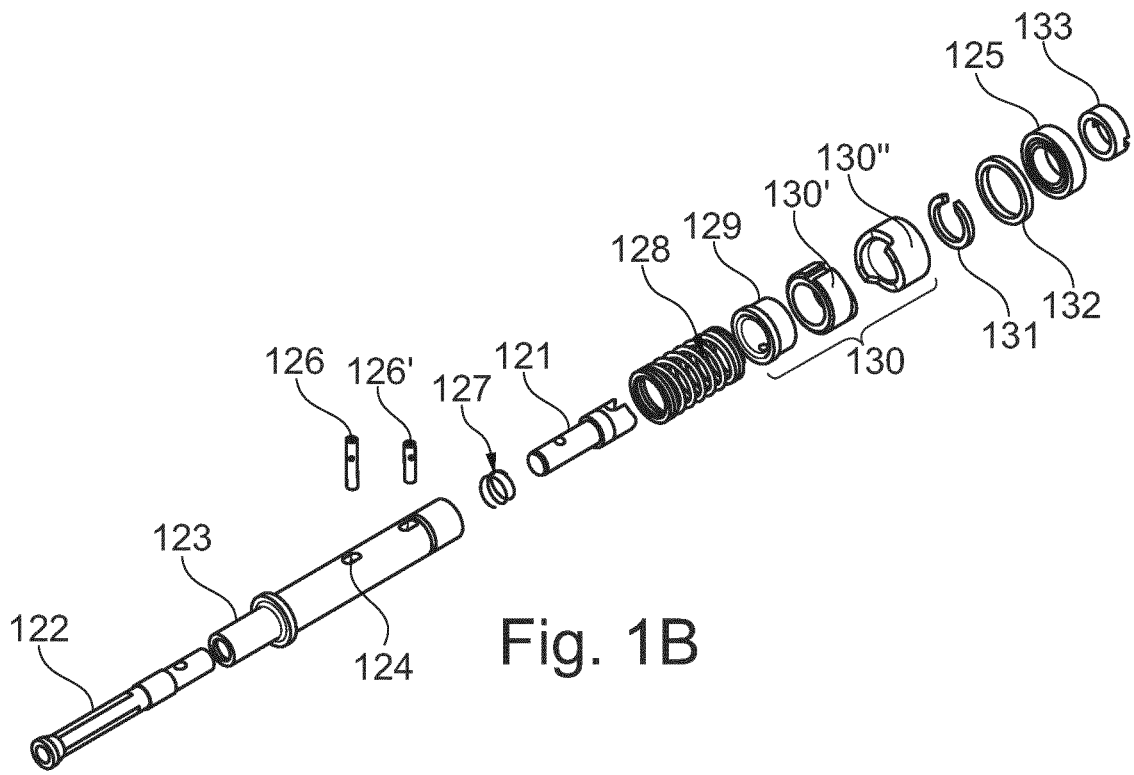

FIG. 1A shows an illustration as an overview of the rotary clamping device 120 according to the invention, and FIG. 1B shows the rotary clamping device 120 in an exploded illustration. The rotary clamping device 120 has a spindle sleeve 123 which in the direction of the processing end 103 contains a, collet chuck 122, and in the direction of the connecting end of the handpiece 100 contains a coupling 121. The coupling 121 is mounted in the spindle sleeve 123. The collet chuck 122 and the coupling 121 are connected to the spindle sleeve 123 by means of fastening means 126, 126', and resiliently mounted by way of a compression spring 127 and a tension spring 128. Clamping sleeves from stainless steel have been utilized as the fastening means 126, 126' in the embodiment shown here. The rotary clamping device 120 furthermore has a release unit 130 for tensioning and relaxing the collet chuck 122. The release unit 130 is composed of two parts, a sliding sleeve 130' and the rotary sleeve 130". The rotary clamping device according to the invention makes it possible to clamp a rotary tool or release the latter for replacing in a simple manner. It can be readily seen that the sliding sleeve 130' and the rotary sleeve 130" have in each case mutually opposite congruent helicoids with identical gradients. By rotating the rotary sleeve 130" the rotary sleeve 130" and the sliding sleeve 130' are mutually twisted and the sliding sleeve 130' is axially displaced according to the gradient of the helicoids. The collet chuck 122 in the interior of the spindle sleeve 123 is connected to the tensioning sleeve 129 by means of a clamping sleeve 126, said tensioning sleeve 129 being disposed externally on the spindle sleeve 123. The spindle sleeve 123 for this purpose in the axial direction has an elongate bore 124 in which the clamping sleeve 126 is guided. The tensioning sleeve 129 serves for receiving the tension spring 128 and for transmitting the axial displacement, triggered by the release unit 130, to the collet chuck 122.

In a rotating movement of the rotary sleeve 130" anaxial displacement of the tensioning sleeve 129 and of the collet chuck 122 arises in the spindle sleeve 123 (indicated by the double arrow at the collet chuck 122), said axial displacement acting counter to the spring force of the tension spring 128. When the helicoids of the sliding sleeve 130' and of the rotary sleeve 130" are mutually rotated out of the position of the greatest overlap by the rotating movement of the rotary sleeve 130", the overlap and thus the contact face of the helicoids is decreased and the tensioning sleeve 129 and the collet chuck 122 in the spindle sleeve 123 is pushed in the direction of the processing end 103 of the handpiece 100 according to the invention. As a result thereof, the collet chuck 122 relaxes and a rotary tool (not shown) in the collet chuck 122 is released. The rotary tool can now be removed and replaced. If the rotating movement of the rotary sleeve 130" takes place in the opposite direction, that is to say if the helicoids of the sliding sleeve 130' and of the rotary sleeve 130" are pushed on top of one another again in the direction of the largest overlap, the clamping ring 129 and the collet chuck 122 in the spindle sleeve 123 during this procedure are moved in the direction of the connecting end 101 of the handpiece 100 according to the invention. As a result thereof, the collet chuck 122 closes and a rotary tool can be fixedly clamped and secured. In order for the rotating movement of the rotary sleeve 130" be guaranteed, the latter preferably has an entrainment pin 146 which can be introduced into an opening 163 of the rotary sleeve 130" provided to this end. This entrainment pin 146 can be, for example, a metal pin or a metal bolt which is screwed into an opening 163 of the rotary sleeve 130" provided to this end. In order for the rectilinear movement of the sliding sleeve 130' to be guaranteed, the sliding sleeve 130' preferably has a groove 164 in which a guide pin 165 is guided in the rectilinear axial movement of the collet chuck 122. As a result of this design of the sliding sleeve 130' it is ensured that the latter is not conjointly rotated while a rotating movement is carried out on the rotary sleeve 130". Contact between the stationary sliding sleeve 130' in the release unit 130 and the clamping ring 129 in the rotating rotary clamping device 120 during operation is prevented with the aid of the restoring spring 144 which on the inside is supported in relation to the bearing sleeve 140 and thus tensions the sliding sleeve 130' in relation to the rotary sleeve 130". During operation, the release unit is situated in the initial position, that is to say that the mutually contacting helicoids of the rotary sleeve 130" and of the sliding sleeve 130' completely overlap. The dimensions of the elongate bore 124 in the spindle sleeve 123 causes a delimitation of the path of the clamping ring 129, so that a sufficient gap between the stationary sliding sleeve 130' and the rotating clamping ring 129 is ensured in the position described.

The rotary clamping device 120 in the direction of the connecting end 101 of the handpiece 100 furthermore has a Seeger locking ring 131, a compensation ring 132 and a slotted nut 133 for fastening the ball bearing in the spindle sleeve 123. It can be readily seen that the rotary clamping device 120 in the direction of the connecting end 101 of the handpiece 100 has a dog clutch 121 which by means of the clamping sleeve 126' and a compression spring 127 is connected to the spindle sleeve 123 as to be able to move axially. Said dog clutch 121 is suitable to be brought to releasably interact with a corresponding counterpart of the motor shaft 111 of the electric drive motor 110 of the handpiece 100.

Figure 2A:
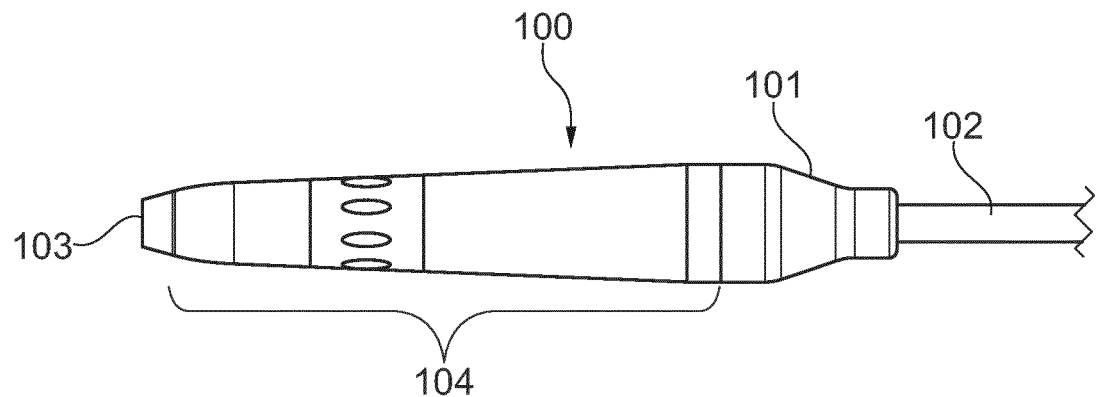
FIG. 2 shows different embodiments of the handpiece according to the invention for a medical or cosmetic processing device.

FIG. 2A shows the handpiece 100 according to the invention in the embodiment of a spray handpiece. The spray handpiece has a housing 104, a connecting end 101, and a processing end 103. The connection line 102 which supplies the spray handpiece with electricity and in which supply lines for water and compressed air for a spray fluid are contained, are situated at the connecting end. The connecting end 101 can furthermore be equipped with light emitting components, as a result of which an illumination function can be implemented at the processing end 103 with the aid of light conductors 156.

Figure 2B:
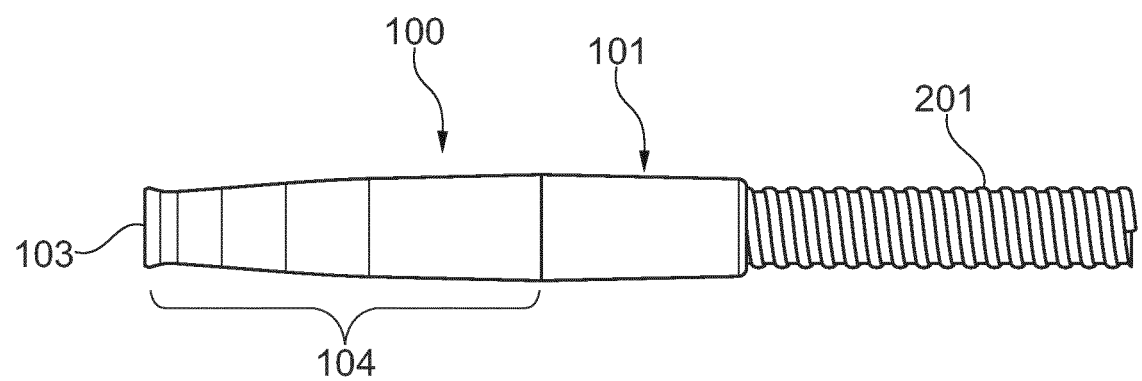

FIG. 2B shows the handpiece 100 according to the invention in the embodiment of a vacuum handpiece. The vacuum handpiece has a housing 104, a connecting end 101, and a processing end 103. Suction hose, or a vacuum hose, respectively, which is connected to a corresponding suction pump (not shown) is attached to the connecting end 104. The vacuum handpiece is constructed such that during operation grinding dust and abrasion which result at the end of processing, are suctioned through the entire handpiece 100 into the vacuum hose 201.

FIG. 3 shows further details of the construction of the handpiece 100 according to the invention in the embodiment as is spray handpiece. The rotary clamping device 120 is mounted in a bearing sleeve 140 of the housing 104 of the handpiece 100, wherein the rotary clamping device 120 in the direction of the processing end 103 and in the direction of the connecting end 101 of the handpiece 100 is in each case locked and mounted by means of ball bearing 125 and 143, a crimp washer 141, a compensation ring 142 and threaded pens 147. The bearing sleeve 140 has an elongate bore 145 for receiving an entrainment pin 146 which is connected to the rotary clamping device 120 in the interior of the bearing sleeve 140. The direction and the extent of the rotating movement of the rotary clamping device 120 is established as a result of the disposal of the entrainment pin 146 in the elongate bore 145, and as a result of the dimensions of the elongate bore 145.

The bearing sleeve 140 in the direction of the connecting end 101 has a motor-guiding sleeve 148 as well as means for coupling or decoupling, respectively, the handpiece to/from the connecting end, said means here being embodied as a spring sleeve 149, a latching member 150 having balls 151, and a seal, the latter here embodied as an O-ring 152.

The handpiece 100 configured as a spray handpiece furthermore has devices for conducting water and compressed air and optionally light. The conduction of water and compressed air takes place by way of ducts provided to this end (water duct 158 and duct 159). The ducts for water 158 and 159 in the embodiment shown here are releasably connected to a coupling ring 161. The conduction of light preferably takes place by way of light conductors such as, for example, a glass fiber rod 156. The ducts 158 and 159 for conducting water, compressed air and the light conductors 156 at the processing end 103 of the handpiece 100 open into a nose 155 which has seals 153, 154 as well as an air nozzle 105' and a water nozzle 106'. The light conductors 156 likewise open into this nose 155. The means for conducting water and compressed air in the interior of the housing 104 of the handpiece 100 are configured as capillary tubes 157 and are guided past the bearing sleeve 140 on the outside of the latter. A connection to the ducts 158 and 159 are established by way of tube connectors 160 which are situated on the coupling ring 161. The same applies to the light conductors 156. The connecting end 101 which is connected to the connection line 102 contains corresponding appliances by way of which the means for conducting water (157, 158), light (156) and compressed air (157, 159) can be connected such that the conduction of water, light and compressed air from the connection line 102 up to the nose 155 and to the nozzles 105', 106', that is to say from the connecting end 101 up to the processing end 103 of the handpiece 100, is guaranteed. Such a means can be, for example, a multiple coupling element in which individual couplings for connecting supply lines for water, compressed air, electricity and light, with the means provided therefor for conducting the respective media through the handpiece, are contained in a bundled manner. However, in the embodiment shown here, the handpiece contains a dedicated component for generating light, specifically a printed circuit board 162 having LEDs. The light of the LEDs by means of the glass fiber rods 156 is directed from the printed circuit board 162 to the processing end 103 of the handpiece 100.

FIG. 4 shows further details of the construction of the handpiece 100 according to the invention in the embodiment as a spray handpiece. The housing 104 in the direction of the processing end 103 has a front sleeve 170, and in the direction of the connecting end 101 a rear sleeve 171. A central sleeve 172 is rotatably disposed between the front sleeve 170 and the rear sleeve 171. One O-ring 173 is in each case disposed as a sealing element between the front sleeve 170 and the central sleeve 172 and between the rear sleeve 171 and the central sleeve 172. The entrainment pin 146 engages in a depression which is provided to this end in the interior of the central sleeve 172. The collar chuck 122 is able to be tensioned or released by rotating the central sleeve 172. As a result thereof, a rotary tool 210 can be clamped or released. The central sleeve 172 in the embodiment shown here has recess grips 174. As a result, the handling of the handpiece 100 according to the invention is improved.

FIG. 4 furthermore shows the motor 110 of the rotary drive unit having the motor shaft 111. It can be readily seen that the motor shaft 111 forms a correspondingly shaped counterpart for the dog clutch 121 of the rotary clamping device 120. The motor is fastened in the handpiece 100 by a retaining ring 180, an O-ring 181 and a spacer sleeve 182. The connecting end 101 has further fastening means such as hexagonal socket head screws 184, as well as a plug connection 185 and insulated bushes 186. A hose locking bush 187 is used for fastening the connection line 102. The connecting end 101 is protected by a screw cap 189.

Figure 5:
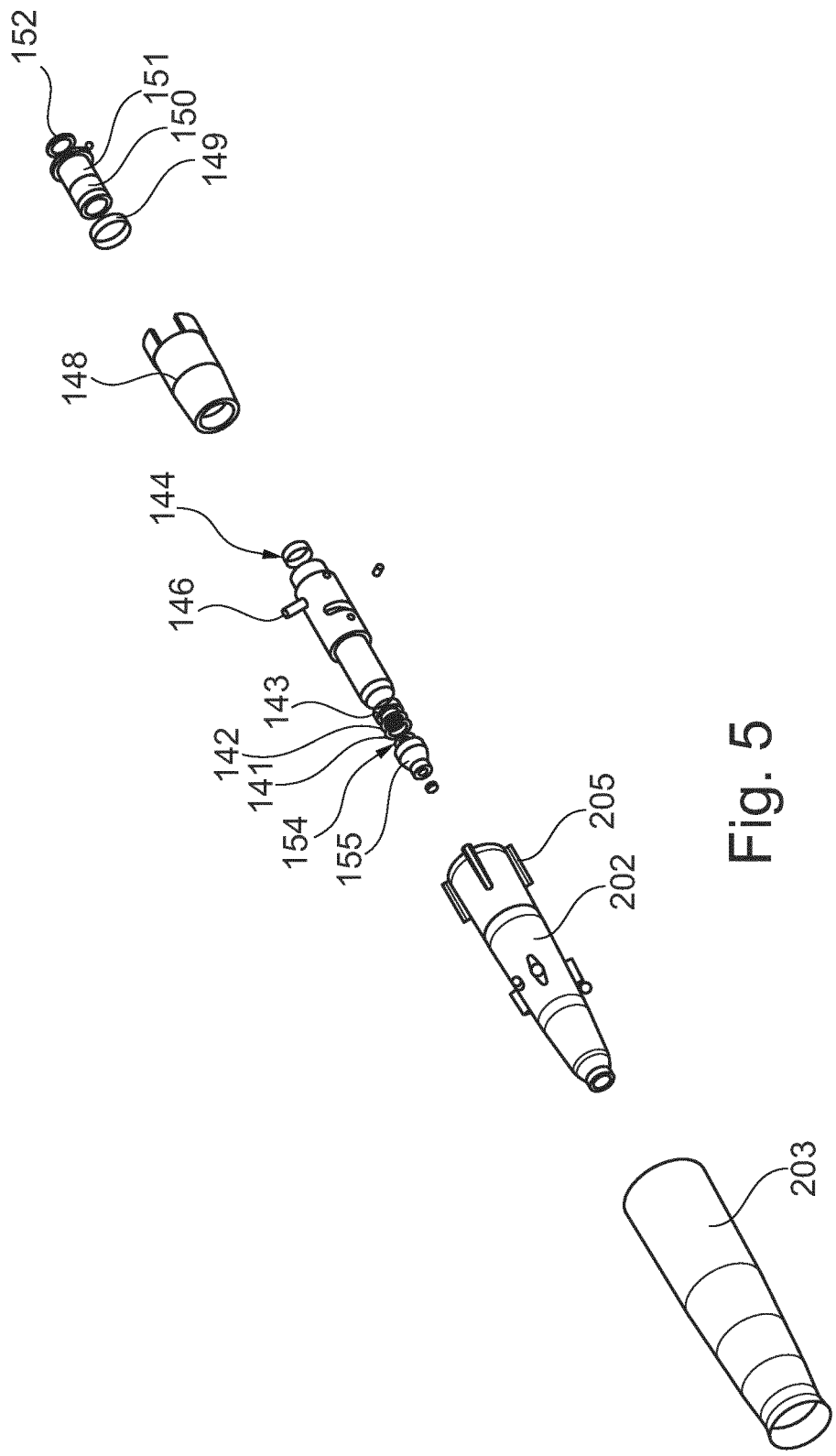
FIG. 5 shows details of the construction of a vacuum handpiece.

FIG. 5 shows further details of the construction of the handpiece 100 according to the invention in the embodiment as a vacuum handpiece. A vacuum hose connector 200 for connecting a suction hose 201 is provided at the connecting end 101. The vacuum handpiece has an inner sleeve 202 in which the bearing sleeve 140 with the rotary clamping device 120 is accommodated. The entrainment pin 146 of the rotary clamping device 120 engages in a depression which is provided to this end in the interior of the inner sleeve 202. The vacuum handpiece has an outer sleeve 203 which in the interior contains elements which interact with the latching elements 204 and entrainment elements 205 on the external side of the inner sleeve 202, as a result of which the outer sleeve 203 is able to be anchored to the inner sleeve 202. The collar chuck 122 is able to be tensioned or released by rotating the outer sleeve 203. As a result, a rotary tool 210 can be clamped or released.

Figure 6:
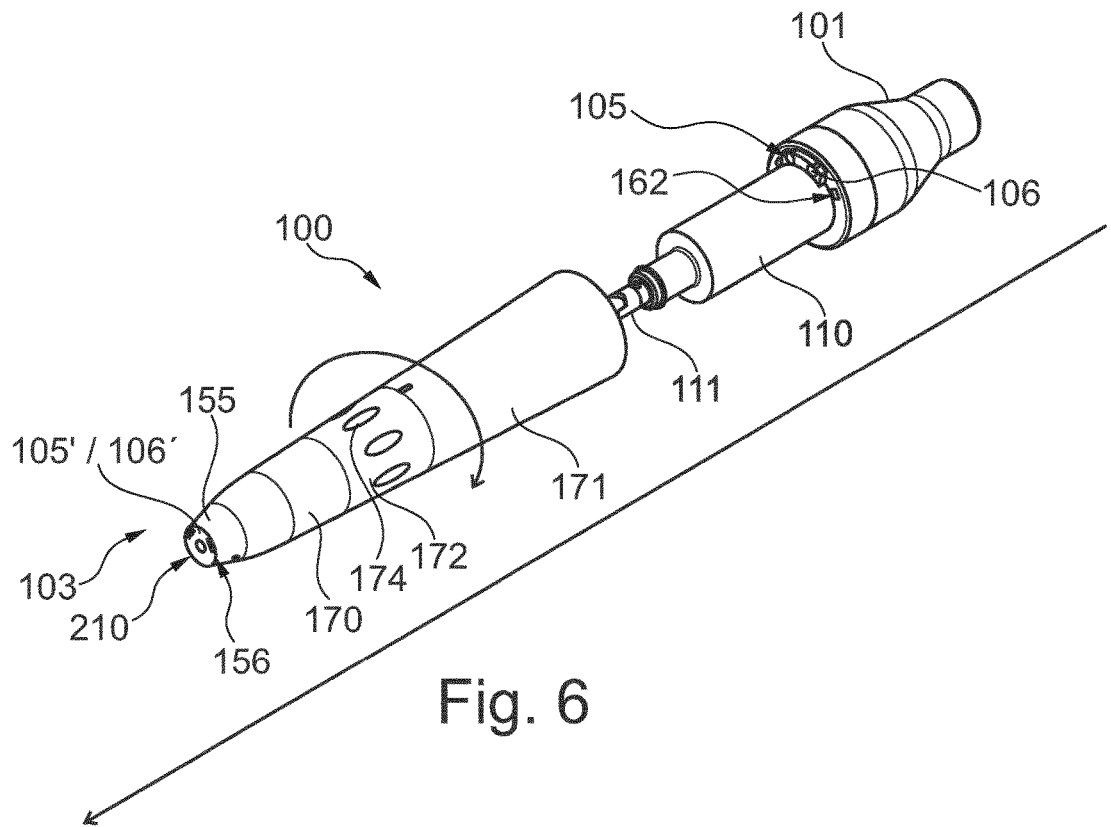
FIG. 6 shows the basic modules of a spray handpiece.

FIG. 6 shows a further view of the construction of the spray handpiece 100 having the connecting end 101. The motor 110 with the motor shaft 111, upon decoupling the housing of the handpiece 100, remains on the connecting end 101. An air connection 105, a water connection 106 and the printed circuit board with LEDs 162 are situated at the connecting end 101. To be seen is the three-part housing, comprising a front sleeve 170, a central rotatable sleeve 172, and a rear sleeve 171. The central rotatable sleeve for improved handling, in particular when clamping and unclamping a rotary tool, is provided with recess grips 174. The nose 155 which have spray nozzles for air 105' and for water 106', as well as an exit for the light conductors 156, is situated in the direction of the processing end 103. A rotary tool 210 can be situated at the processing end 103. The arrow running from the connecting end 101 to the processing end 103 indicates that water and air for the spray device, as well is light, are conducted through the entire handpiece 100. Because the motor 110 when releasing the handpiece 100 remains on the connecting end 101, the releasable part of the handpiece 100 can be advantageously cleaned and sterilized, in particular sterilized by heat or steam.

Figure 7:
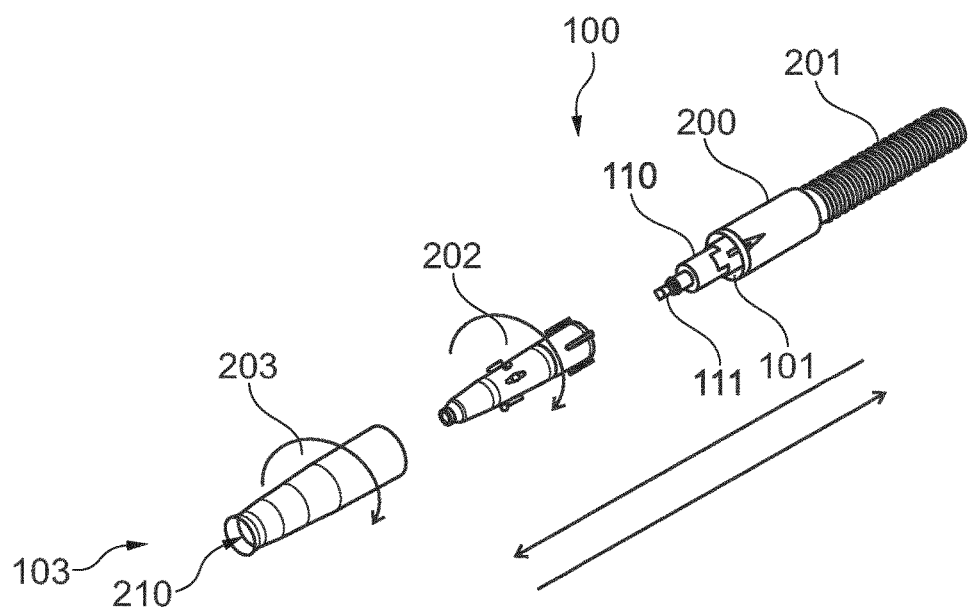
FIG. 7 shows the basic modules of a vacuum handpiece.

FIG. 7 shows a further view of the construction of the vacuum handpiece 100 having the vacuum hose 201 which is connected to a vacuum hose connector 200 at the connecting end 101 of the handpiece 100. In this embodiment the motor 110 also remains on the connecting end 101 when the front part of the handpiece 100, here formed by the outer sleeve 203 and the inner sleeve 202, are removed from the connecting end 101. The inner sleeve 202 contains the rotary clamping device 120 according to the invention. The continuous arrow from the processing end 103 in the direction of the connecting end 101 indicates the profile of the air as well as of grinding dust and abrasion which during the use of the handpiece 100 are suctioned from the processing end 103 through the entire handpiece into the vacuum hose 201. Because the motor 110 when releasing the handpiece 100 remains on the connecting end 101, the releasable parts 203, 202 of the handpiece 100 can be advantageously cleaned and sterilized, in particular sterilized by heat or steam.

The handpiece provided by the invention has a plurality of advantages. The rotary clamping device 120 ensures that a rotary tool can be clamped in an optimal manner but also be released from the handpiece 100 in a simple manner by the user. As a result of the handpiece 100 being able to be released from the connecting end 101 in such a manner that the motor 110 remains connecting end, it is ensured that that part of the handpiece 100 on which contamination arises as a result of the use of the handpiece 100 in the cosmetic or medical sector can be cleaned and sterilized in an optimal manner, in particular sterilized by heat or steam.

LIST OF REFERENCE SIGNS

100 Handpiece
101 Connecting end
102 Connection line
103 Processing end
104 Housing
105 Air connection
106 Water connection
105' Air nozzle
106' Water nozzle
110 Motor
111 Motor shaft
120 Rotary clamping device
121 Coupling, dog clutch
122 Collet chuck
123 Spindle sleeve
124 Elongate bore for collet chuck
125 Ball bearing
126,126' Clamping sleeve, fastening means
127 Compression spring
128 Tension spring
129 Tensioning sleeve
130 Release unit
130' Sliding sleeve
130" Rotary sleeve
131 Seeger locking ring
132 Compensation ring
133 Slotted nut
140 Bearing sleeve
141 Crimp washer
142 Compensation ring
143 Ball bearing
144 Restoring spring
145 Elongate bore
146 Entrainment pin
147 Threaded pin
148 Motor-guiding sleeve
149 Spring sleeve
150 Latching member
151 Balls
152 Seal, O-ring
153 Seal
154 Seal, O-ring
155 Nose
156 Glass fiber rod, light conductor
157 Capillary tube
158 Water duct
159 Air duct
160 Tube connector, hose connector
161 Coupling ring, connecting ring
162 PCB-Board with LEDs
163 Bore, opening
164 Groove
165 Guide pin
170 Front sleeve
171 Rear sleeve
172 central rotatable sleeve
173 Seal, O-ring
174 Recessed grip
180 Retaining ring
181 Seal, O-ring
182 Spacer sleeve
183 PCB contact
184 Hexagonal socket head screw
185 Plug connection
186 Insulating bush
187 Hose-locking bush
189 Screw cap
190 Housing portion for coupling device between housing of the handpiece and the
connecting end
200 Vacuum hose connector
201 Vacuum hose
202 Inner sleeve
203 Outer sleeve
204 Latching elements
205 Entrainment element
210 Rotary tool, receptacle for the rotary tool

The invention claimed is:

1. A handpiece (100) for a medical or cosmetic processing device, having:
a connection line (102) at a connecting end (101);
a housing (104) in which a receptacle space is provided between the connecting end (101) and a processing end (103), a rotary drive unit for driving a rotary tool (210) that is attachable to the processing end (103) being able to be received in said receptacle space,
characterized in that the handpiece (100) is able to be separated from the connecting end (101), wherein the handpiece (100) is designed such that a motor (110) upon decoupling of the housing (104) remains on the connecting end (101);
the handpiece has a rotary clamping device (120) in which the rotary tool (210) is able to be attached; and wherein the rotary clamping device (120) in the direction of the processing end (103) and in the direction of the connecting end (101) of the handpiece (100) is locked and mounted by means of locking elements (141, 142, 147), bearings (125, 143) and springs (144).

2. The handpiece (100) as claimed in claim 1,
characterized in that
the rotary drive unit has a motor (110), preferably an electric motor, and a bearing sleeve (140) in which the rotary clamping device (120) is able to be received and which in the direction of the connecting end (101) by way of a coupling (121) is releasably connected to the motor shaft (111) and which in the direction of the processing end (103) has a collet chuck (122) in which the rotary tool (210) is able to be attached.

3. The handpiece (100) as claimed in claim 2,
characterized in that the rotary clamping device (120) has a spindle sleeve (123) which in the direction of the processing end (103) of the handpiece (100) contains the collet chuck (122) and in the direction of the connecting end (101) of the handpiece (100) contains a coupling (121);
the spindle sleeve (123) is mounted in two bearings (125) and (145);
wherein the collet chuck (122) and the coupling (121) are connected to the spindle sleeve (123) by means of fastening means (126, 126') and are resiliently mounted by way of a compression spring (127) and a tension spring (128).

4. The handpiece (100) as claimed in claim 3,
characterized in that the rotary clamping device (120) furthermore has a tensioning sleeve (129) with a release unit (130) for clamping and relaxing the collet chuck (122), and the rotary clamping device (120) in the direction of the connecting end (101) of the handpiece (100) has seals and locking elements (131, 132, 133) for locking the collet chuck (122), the coupling (121) and the release unit (130) in the spindle sleeve (123).

5. The handpiece (100) as claimed in claim 2, characterized in that
the bearing sleeve (140) in the direction of the connecting end (101) has a motor-guiding sleeve (148) as well as means (149, 150, 151, 152) for coupling or decoupling, respectively, the handpiece (100) to or from the connecting end (101).

6. The handpiece (100) as claimed in claim 2, wherein the coupling (121) is a dog clutch.

7. The handpiece (100) as claimed in claim 1, characterized in that
a rotary sleeve (130") of the rotary clamping device (120) is rotatably mounted in a bearing sleeve (140) of the housing (104) of the handpiece (100).

8. The handpiece (100) as claimed in claim 7, characterized in that
the bearing sleeve (140) has an elongate bore (145) for receiving an entrainment pin (146) which is connected to the rotary sleeve (130") of the rotary clamping device (120) in the interior of the bearing sleeve 140), wherein the direction and the extent of the rotating movement of the rotary sleeve (130") of the rotary clamping device (120) is able to be established by the disposal of the entrainment pin (146) in the elongate bore (145) and by the dimensions of the elongate bore (145).

9. The handpiece (100) as claimed in claim 8, characterized in that
a sliding sleeve (130') and the rotary sleeve (130") are designed such that the rotating movement that is able to be generated on the rotary sleeve (130") is able to be converted to an axial movement of the collet chuck (122) and, as a result thereof, the collet chuck (122) is able to be tensioned or released.

10. The handpiece (100) as claimed in claim 1, characterized in that
the handpiece (100) is configured as a spray handpiece and has devices for conducting water and compressed air (105, 106, 158, 159, 157, 105', 106) and optionally light (183, 162, 158).

11. The handpiece (100) as claimed in claim 10, characterized in that
the housing (104) in the direction of the processing end (103) has a front sleeve (170), and in the direction of the connecting end (101) has a rear sleeve (171), and a central sleeve (172) is disposed so as to be rotatable between the front sleeve (170) and the rear sleeve (171), wherein a sealing element (173) is in each case disposed between the front sleeve (170) and the central sleeve (172), and the rear sleeve (171) and the central sleeve (172), wherein an entrainment pin (146) engages in a depression defined by the central sleeve (172), a collet chuck (122) associated with rotary clamping device (120) is adapted to be tensioned or released, and a rotary tool (210) can be clamped or released, by rotating the central sleeve (172).

12. The handpiece (100) as claimed in claim 11, characterized in that
the central sleeve (172) has a recessed grip (174).

13. The handpiece (100) as claimed in claim 1, characterized in that
the handpiece (100) is configured as a vacuum handpiece, and at the connecting end (101) has a vacuum hose connector (200) for connecting a suction hose (201).

14. The handpiece (100) as claimed in claim 13, characterized in that
the handpiece (100) has an inner sleeve (202) in which a bearing sleeve (140) associated with the rotary clamping device (120) is accommodated, and an entrainment pin (146) engages a depression defined by the inner sleeve (202).

15. The handpiece (100) as claimed in claim 14, characterized in that
the handpiece (100) has an outer a sleeve (203) which contains elements which interact with devices (204, 205) provided to this end on the external side of the inner sleeve (202), as a result of which the outer sleeve (203) is able to be anchored to the inner sleeve (202), and wherein a collet chuck (122) associated with rotary claiming device (120) is adapted to be tensioned or released, and the rotary tool (210) can be clamped or released, by rotating the outer sleeve (203).

16. The handpiece (100) as claimed in claim 1, characterized in that
the motor (110) is connected to the connecting end (101), and the housing (104) of the handpiece (100) furthermore has a housing portion (190) for a coupling installation by way of which the handpiece (100) can be released from the connecting end (101) or connected to the connecting end (101).

17. The handpiece (100) as claimed in claim 1, wherein detachable parts of the handpiece (100) are made of materials which are sterilizable by heat or steam.

18. The handpiece (100) as claimed in claim 17, wherein detachable parts of the handpiece (100) are made of stainless steel.

19. The handpiece (100) as claimed in claim 17, wherein detachable parts of the handpiece (100) are made of a heat-tolerant plastic.

20. The handpiece (100) as claimed in claim 19, wherein the heat-tolerant plastic is polyetheretherketone (PEEK).

* * * * *